United States Patent
Strimpel et al.

(10) Patent No.: US 8,847,176 B1
(45) Date of Patent: Sep. 30, 2014

(54) SYSTEM FOR DETECTING FLUORESCING SUBSTANCES ON NON-FLUORESCING MATERIAL USING THE HUMAN EYE

(75) Inventors: Nathan Strimpel, Milan, MI (US);
Mark A. Imbrock, Sylvania, OH (US);
Jeffrey A. Simpson, Wayne, NE (US)

(73) Assignee: EDTM, Inc., Toledo, OH (US)

( * ) Notice: Subject to any disclaimer, the term of this patent is extended or adjusted under 35 U.S.C. 154(b) by 63 days.

(21) Appl. No.: 13/594,850

(22) Filed: Aug. 26, 2012

Related U.S. Application Data

(60) Provisional application No. 61/527,784, filed on Aug. 26, 2011.

(51) Int. Cl.
*G01N 21/64* (2006.01)

(52) U.S. Cl.
CPC .................................. *G01N 21/64* (2013.01)
USPC ..................................................... 250/461.1

(58) Field of Classification Search
USPC ................. 250/461.1, 302, 561, 360, 372
See application file for complete search history.

(56) References Cited

U.S. PATENT DOCUMENTS

| | | | |
|---|---|---|---|
| 4,323,785 A | | 4/1982 | McComb et al. |
| 4,532,429 A | * | 7/1985 | Horikawa ................ 250/559.36 |
| 5,512,758 A | * | 4/1996 | Kobayashi et al. ........ 250/461.1 |
| 6,683,695 B1 | * | 1/2004 | Simpson et al. .............. 356/632 |
| 7,227,139 B2 | * | 6/2007 | Kram et al. ................... 250/301 |
| 7,369,240 B1 | * | 5/2008 | Abbott et al. ................ 356/429 |
| 7,417,749 B1 | * | 8/2008 | Simpson et al. .............. 356/632 |
| 7,499,165 B2 | * | 3/2009 | Simpson et al. .............. 356/407 |
| 7,551,274 B1 | * | 6/2009 | Wornson et al. ........... 356/239.1 |
| 7,652,760 B1 | * | 1/2010 | Simpson et al. ........... 356/239.1 |
| 7,679,063 B2 | * | 3/2010 | Hoffman et al. .............. 250/375 |
| 8,242,461 B2 | * | 8/2012 | Rosicke et al. ............. 250/458.1 |
| 8,316,333 B2 | | 11/2012 | Darsow et al. |
| 2006/0054843 A1 | * | 3/2006 | Simpson et al. ......... 250/559.27 |
| 2006/0215162 A1 | * | 9/2006 | Shannon et al. .............. 356/419 |
| 2007/0272873 A1 | * | 11/2007 | Jadrich et al. ............ 250/370.11 |
| 2008/0019478 A1 | * | 1/2008 | Poteet et al. ..................... 378/45 |
| 2008/0020483 A1 | * | 1/2008 | Nishigaki et al. ............. 436/172 |
| 2010/0252747 A1 | * | 10/2010 | Nakano et al. ............. 250/458.1 |

\* cited by examiner

*Primary Examiner* — David Porta
*Assistant Examiner* — Taeho Jo
(74) *Attorney, Agent, or Firm* — MacMillan, Sobanski & Todd, LLC

(57) ABSTRACT

An apparatus for detecting a fluorescing substance on a test material includes a light source configured to direct light energy toward the test material, and one or more display features configured to display fluorescing light from the test material. When light from the light source contacts the fluorescing material, display features allows the fluorescing material to project a fluorescing glow into an ambient environment near the apparatus.

18 Claims, 5 Drawing Sheets

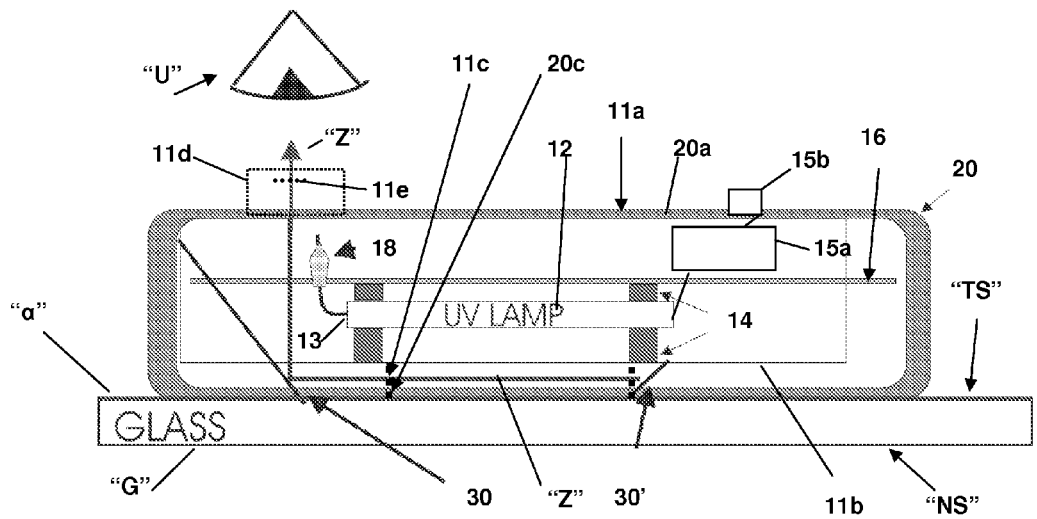
FIG. 3
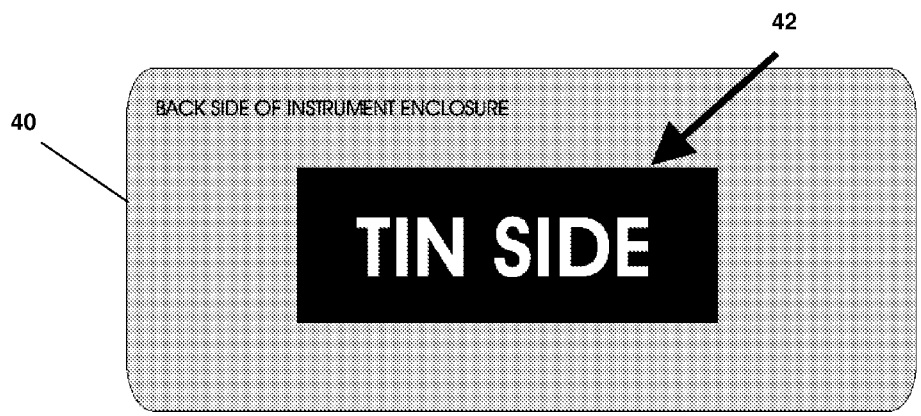
FIG. 4A
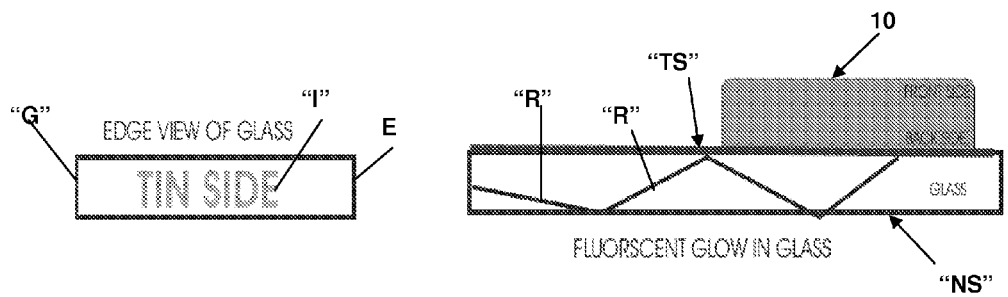

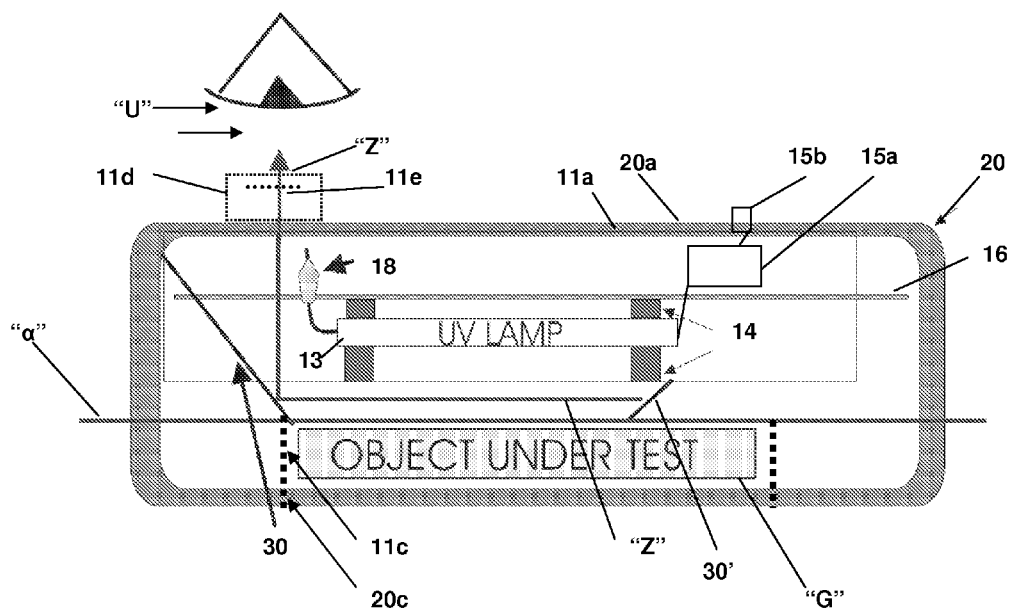
FIG. 4B
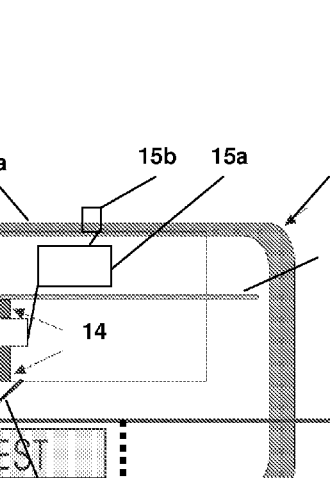
FIG. 4C
FIG. 5A
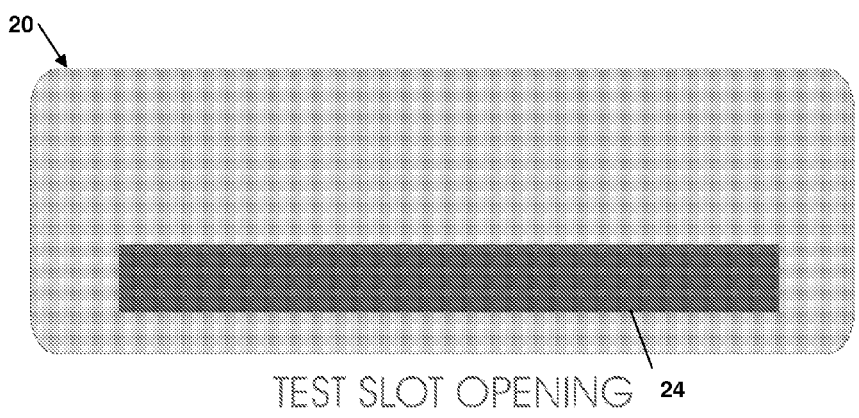
FIG. 5B

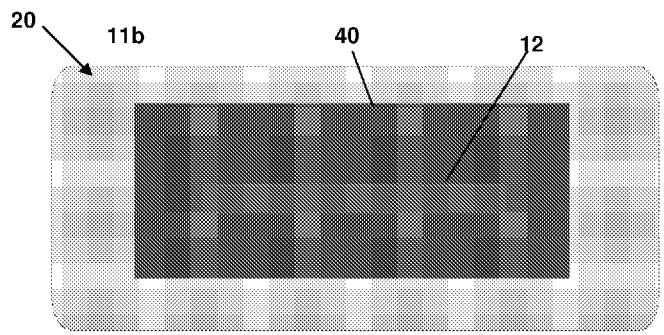
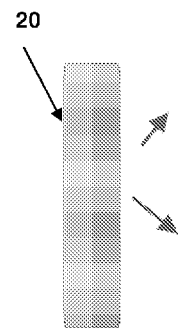
BLACK VIEWING AREA SIGNIFICANTLY LARGER THEN UV LAMP SOURCE
FIG. 6A
FIG. 6B
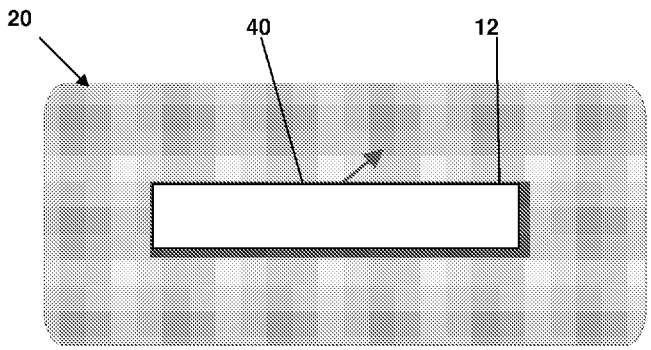
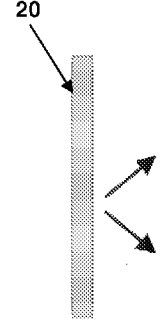
BLACK VIEWING AREA CLOSE TO UV LAMP SOURCE SIZE, MORE FLUORESCING LIGHT ENTERS THE BOOT MATERIAL SO THE USER SEE A GREATER CHANGE IN COLOR OR SHADE
FIG. 6C
CLOSER TO UV SOURCE, THINNER MATERIAL
FIG. 6D

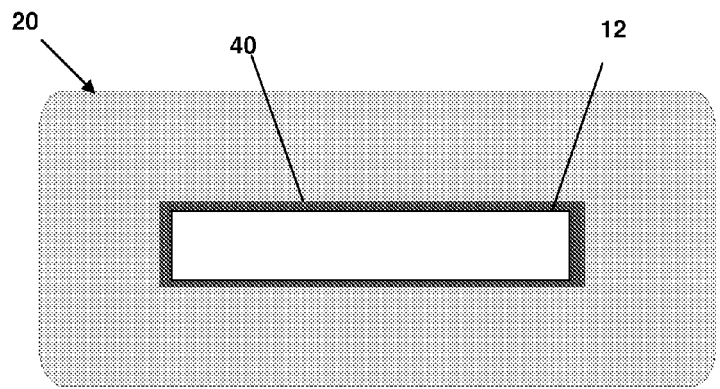
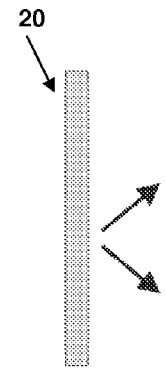
FIG. 7A
FIG. 7B
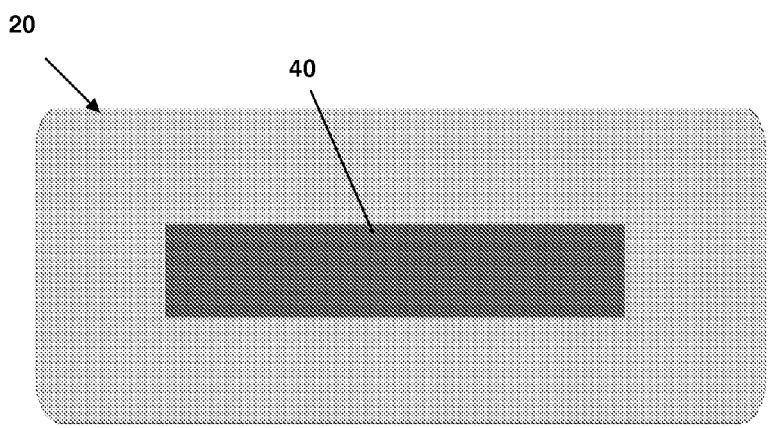
FIG. 7C
FIG. 7D

SYSTEM FOR DETECTING FLUORESCING SUBSTANCES ON NON-FLUORESCING MATERIAL USING THE HUMAN EYE

CROSS-REFERENCE TO RELATED APPLICATION

The present invention claims the benefit of the provisional patent application Ser. No. 61/527, 784 filed Aug. 26, 2011, which is expressly incorporated herein by reference.

TECHNICAL FIELD

This invention generally relates to a system for detecting traces of a fluorescing substance on a non fluorescent material. The fluorescing substance may be metal or metal oxide on a glass surface using the human eye for detection. The invention also can be used to detect other fluorescing materials on other substrates as well.

BACKGROUND

Common flat glass is called float glass because during the manufacturing process the glass floats on the top of a molten tin bath. The tin bath leaves small traces of metal or metal oxides on the surface of the glass that was in contact with the molten bath. Some glass processors that laminate or apply coatings to the glass require the knowledge of which side of the float glass was contacting the molten tin bath. This is especially important to glass processors when the coatings being applied have a reaction with the residue traces of metal or metal oxides, thereby changing the characteristics of the coating being applied.

Also, in the glass coating industry, there also are numerous applications where spectral reflective coatings are applied to a transparent surface. Some of these applications include flat glass, windows, LCD screens, solar cell panels, thermal efficient films, as well as many other plastic and glass applications. During the processing of these flat materials, it is often desirable to have an apparatus that is able to detect the presence and location of the "invisible" coatings. The coatings may be located on one or both surfaces of a single piece of transparent material, or on one or more surfaces of multiple pieces of transparent material built into an assembly, separated by a known transparent media such as a gas.

Also, in the building industry it is sometime necessary to identify if a completed product, such as a window, is made of a transparent glass having coating applied to a surface thereof.

The standard method of detecting the tin surface of glass is to cause the tin surface to fluoresce, resulting in a white visible glow that can be seen by human eyes. This test is performed by having the user place a UV light source close to the tin surface of the float glass. This method has been used for over 20 years and requires essentially three components: (1) a UV lamp, (2) an optical filter that passes the UV light but reflects the visible fluorescing light which helps viewing, and (3) the human eye which views the resulting glow. There have been no known improvements in this human eye method during the period of time.

Sensors have been added to the process to allow electronic inspection of the glow; for example, U.S. Pat. No. 4,323,785 describes discloses one method for detecting the presence and locations of transparent metallic oxides on glass sheets. This process uses ultraviolet lamps to cause the metallic oxide to fluorescence and the resulting glow is detected with sensors. This process requires large lamps, which generally must be mounted within an extremely close distance of the material under test.

Another device with a sensor utilizes a UV LED and a light sensor to sense the fluorescing glow. The results are indicated by illuminating an LED when placed on the tin surface of the glass.

In the past, users have had difficulty in obtaining a reading due to the unreliability of the prior devices. Such devices were difficult to use in most work/test environments due to the presence of ambient light in the work environment. In the past, it was generally understood that, during use of an apparatus for detecting a tin side of a glass, the user often needed to angle the apparatus away from the glass slightly and look under the apparatus in order to see whether there was a fluorescing glow from the tin side, or whether there was a lack of glow (non-tin side).

In order to be able to obtain an accurate reading, users sometimes placed their eye down close to the UV lamp, thus endangering their vision by exposure to UV light.

There is a continuing need for an improved, reliable and efficient method and device to accurately detect fluorescing material on various media using the human eye.

Therefore, it is desirable to have a surface coating detection apparatus that can be implemented that will easily show which surface has a coating and/or fluorescing material. It is also desirable to have a portable apparatus that can be used in the field by workers to quickly and accurately make such detections.

BRIEF SUMMARY OF THE INVENTION

In a first broad aspect, there is provided herein an apparatus for detecting a fluorescing substance on a test material, comprising a light source configured to direct UV light energy toward the test material, and a fluorescing light responsive covering material capable of responding to the UV light directed at the test material.

In a particular aspect, there is provided herein an apparatus for detecting a fluorescing substance on a test material having: a light source configured to direct light energy toward the test material, and a display feature configured to display fluorescing light from the test material. In use, the light contacts the fluorescing material, display features allow the fluorescing material to project a fluorescing glow into an ambient environment near the apparatus.

In certain embodiments, the display feature is configured to allow at least a portion of the light to pass through and into the test material.

In certain embodiments, the display feature comprises a stenciled area positioned adjacent to the light source.

In certain embodiments, the display feature is configured to allow a glowing image to be projected onto the test material.

In certain embodiments, the display feature is configured to allow viewing of a glowing image which is transferred through the test material and viewed in an edge surface of the test material.

In certain embodiments, the apparatus further includes one or more shock-absorbing resilient materials positioned adjacent to and/or in contact with the light source.

In certain embodiments, the light source includes one or more terminal insertion sockets operatively connecting the light source to a power source.

In certain embodiments, the apparatus further includes a shock-absorbing covering material that at least partially encloses the apparatus.

In certain embodiments, the covering material is comprised of a silicone rubber material.

In certain embodiments, the covering material is at least partially comprised of material that illuminates when exposed to visible fluorescing light.

In certain embodiments, the covering material is at least partially coated with a material that illuminates when exposed to visible fluorescing light.

In certain embodiments, the covering material allows the fluorescing light to be absorbed, causing the covering material to change shade or color.

In certain embodiments, the apparatus includes a housing having an opening configured to allow an edge of the test material to be inserted into the opening.

In certain embodiments, the apparatus has a housing having a viewing window on a front face thereon configured to a view a fluorescing glow.

In certain embodiments, the apparatus further includes one or more reflective surfaces positioned within the apparatus positioned to project a fluorescent image to a front face of the apparatus.

In certain embodiments, the reflective surface comprises one or more of: a mirror, a prism, a fiber optics, a polished metal, and combinations thereof.

In certain embodiments, the apparatus further includes one or more materials placed in an optical path of the fluorescent image which allows an index of refraction of the test material to be optically matched to an index of refraction of the reflective surface.

In certain embodiments, the apparatus includes a housing defining a light source aperture, and having an area partially or substantially surrounding the light source aperture. The surrounding area can have defined edges that are close in proximity to the light source aperture. Also, in certain embodiments, the defined edges can be configured to form a framed, or definitive edge, to the fluorescing glow.

In certain embodiments, the apparatus includes a source of power operatively connected to the light source capable of providing pulsed energy, causing the difference between the fluorescing glow and lack thereof to be easier to detect with the eye.

In certain embodiments, the power source is configured to provide either continual pushes using a momentary power switch, or using a microprocessor control.

In another aspect, there is provided herein an apparatus for detecting a fluorescing substance on a test material having: a light source configured to direct light energy toward the test material, and one or more shock-absorbing resilient materials positioned adjacent to and/or in contact with the light source.

In another aspect, there is provided herein an apparatus for detecting a fluorescing substance on a test material having: a light source configured to direct light energy toward the test material, and one or more terminal insertion sockets operatively connecting the light source to a power source.

In another aspect, there is provided herein an apparatus for detecting a fluorescing substance on a test material having: a light source configured to direct light energy toward the test material, and a shock-absorbing covering material that at least partially encloses the apparatus.

In certain embodiments, the covering material is comprised of a silicone rubber material.

In certain embodiments, the covering material is at least partially comprised of material that illuminates when exposed to visible fluorescing light.

In certain embodiments, the covering material is at least partially coated with a material that illuminates when exposed to visible fluorescing light.

In certain embodiments, the covering material allows the fluorescing light to be absorbed, causing the covering material to change shade or color.

In another aspect, there is provided herein an apparatus for detecting a fluorescing substance on a test material having: a light source configured to direct light energy toward the test material, and a shock-absorbing covering material that at least partially encloses the apparatus, where the covering material is at least partially comprised of material that illuminates when exposed to visible fluorescing light.

In another aspect, there is provided herein an apparatus for detecting a fluorescing substance on a test material having: a light source configured to direct light energy toward the test material, and a housing having an opening configured to allow an edge of the test material to be inserted into the opening.

In another aspect, there is provided herein an apparatus for detecting a fluorescing substance on a test material having: a light source configured to direct light energy toward the test material, and a housing having a viewing window on a front face thereon configured to a view a fluorescing glow.

In another aspect, there is provided herein an apparatus for detecting a fluorescing substance on a test material having: a light source configured to direct light energy toward the test material, and one or more reflective surfaces within the apparatus positioned to project a fluorescent image to a front face of the apparatus.

In certain embodiments the reflective surface comprises one or more of: a mirror, a prism, a fiber optics, a polished metal, and combinations thereof.

In certain embodiments the apparatus further includes one or more materials placed in an optical path of the fluorescent image which allows an index of refraction of the test material to be optically matched to an index of refraction of the reflective surface.

In another aspect, there is provided herein an apparatus for detecting a fluorescing substance on a test material having: a light source configured to direct light energy toward the test material, and a housing defining a light source aperture, and having an area partially or substantially surrounding the light source aperture. The surrounding area have defined edges that are close in proximity to the light source aperture, the defined edges being configured to form a framed, or definitive edge, to the fluorescing glow.

In another aspect, there is provided herein an apparatus for detecting a fluorescing substance on a test material having: a light source configured to direct light energy toward the test material, and a source of power operatively connected to the light source capable of providing pulsed energy, causing the difference between the fluorescing glow and lack thereof to be easier to detect with the eye.

In certain embodiments, the power source is configured to provide either continual pushes using a momentary power switch, or using a microprocessor control.

In another aspect, there is provided herein an apparatus for detecting a fluorescing substance on a test material having: a light source configured to direct light energy toward the test material, and at least one of: a display feature configured to display fluorescing light from the test material; wherein, when the light contacts the fluorescing material, display features allows the fluorescing material to project a fluorescing glow into an ambient environment near the apparatus; one or more reflective surfaces within the apparatus positioned to project a fluorescent image to a front face of the apparatus; a housing defining a light source aperture, and having an area substantially surrounding the light source aperture, the surrounding area having defined edges that are close in proximity to the light source aperture, the defined edges being configured to form a framed, or definitive edge, to the fluorescing glow; and, a source of power operatively connected to the light source capable of providing pulsed energy, causing the difference between the fluorescing glow and lack thereof to be easier to detect with the eye.

In certain embodiments, the apparatus further includes one or more of: one or more shock-absorbing resilient materials positioned adjacent to and/or in contact with the light source; one or more terminal insertion sockets operatively connecting the light source to a power source; a shock-absorbing covering material that at least partially encloses the apparatus.

In certain embodiments, the covering material is comprised of a silicone rubber material. In certain embodiments, the covering material is at least partially comprised of material that illuminates when exposed to visible fluorescing light. In certain embodiments, the covering material is at least partially coated with a material that illuminates when exposed to visible fluorescing light. In certain embodiments, the covering material allows the fluorescing light to be absorbed, causing the covering material to change shade or color.

There is provided also herein a method for enhancing the viewing of a fluorescing glow for user discrimination of a fluorescing material on a test material.

Various objects and advantages of this invention will become apparent to those skilled in the art from the following detailed description of the preferred embodiment, when read in light of the accompanying drawings.

BRIEF DESCRIPTION OF THE DRAWINGS

FIG. 3 is a diagrammatic, cross-sectional side-elevational view showing an apparatus according to another embodiment of the invention for detecting a presence or absence of a fluorescing material on a test material, where the apparatus is positioned adjacent a test material depicted as a glass having a tin coating thereon.

FIG. 4A is a diagrammatic view of a back side of a display feature for one or more of the apparatuses shown in FIGS. 1, 2 and 3.

FIG. 4B is a diagrammatic view of an edge of a glass showing a reflected word image therein.

FIG. 4C is a diagrammatic view showing an apparatus according to one embodiment of the invention adjacent a test material having a fluorescing material thereon, and showing angles of reflected light being transmitted therethrough.

FIG. 5A is a diagrammatic, cross-sectional side-elevational view showing an apparatus according to another embodiment of the invention for detecting a presence or absence of a fluorescing material on a test material, where a least a portion of the test material is positioned within the apparatus.

FIG. 5B is a diagrammatic end view of the embodiment shown in FIG. 5A.

FIG. 6A is a diagrammatic view of a bottom surface of an apparatus according to another embodiment of the invention for detecting a presence or absence of a fluorescing material on a test material, where a fluorescing light is in an "on" mode.

FIG. 6B is an end view of the apparatus shown in FIG. 6A.

FIG. 6C is a diagrammatic view of a bottom surface of an apparatus according to another embodiment of the invention for detecting a presence or absence of a fluorescing material on a test material, where a fluorescing light is in an "on" mode but the boot and opening is significantly closer to the UV light source.

FIG. 6D is an end view of the apparatus shown in FIG. 6C.

FIG. 7A is a diagrammatic view of a bottom surface of an apparatus according to another embodiment of the invention for detecting a presence or absence of a fluorescing material on a test material, where a fluorescing light is in an "on" mode.

FIG. 7B is an end view of the apparatus shown in FIG. 7A.

FIG. 7C is a diagrammatic view of a bottom surface of an apparatus according to another embodiment of the invention for detecting a presence or absence of a fluorescing material on a test material, where a fluorescing light is in an "off" mode.

FIG. 7D is an end view of the apparatus shown in FIG. 7C.

DETAILED DESCRIPTION OF THE INVENTION

It is to be understood that the Figures herein are schematic illustrations, and as such, are not shown in cross-section for ease of understanding.

Figure 1:
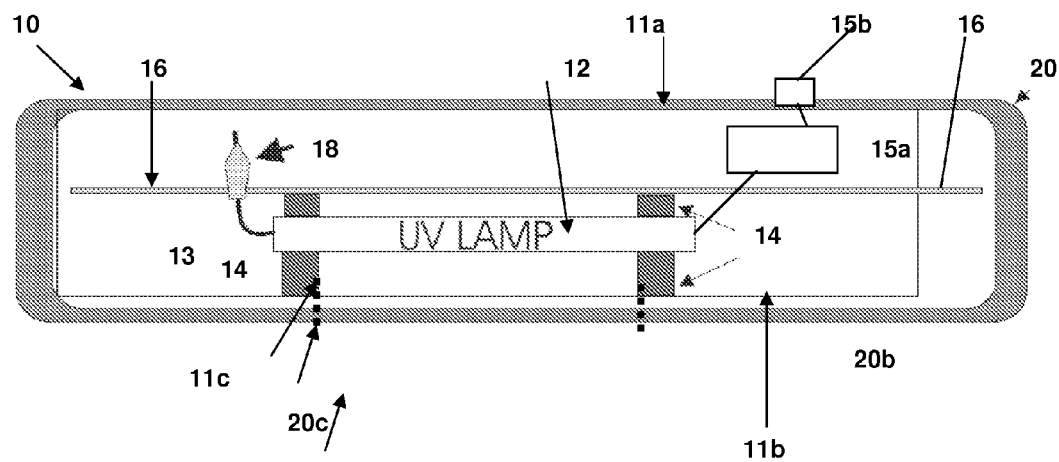
FIG. 1 is a diagrammatic, cross-sectional side-elevational view showing an apparatus according to one embodiment of the invention for detecting a presence or absence of a fluorescing material on a test material.
Figure 2:
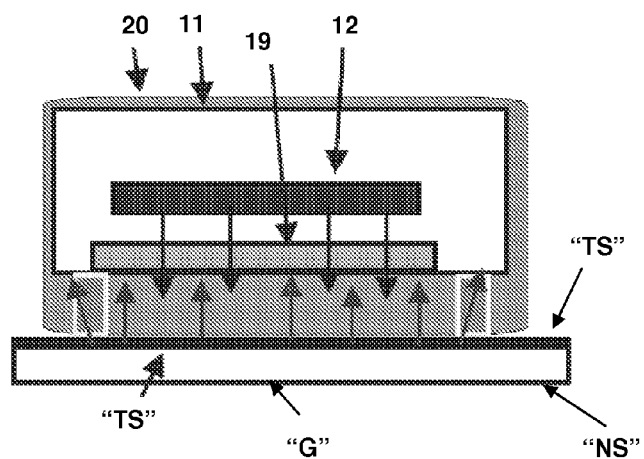
FIG. 2 is a diagrammatic, cross-sectional side-elevational view showing an apparatus according to another embodiment of the invention for detecting a presence or absence of a fluorescing material on a test material.

Referring first to FIG. 1, there is diagrammatically shown a cross-sectional view of an apparatus 10 for detecting materials and/or coatings on a transparent material. The apparatus 10 generally includes a housing 11 having a light source 12 operatively mounted therein (shown herein as a UV light source). For ease of explanation herein, the housing 11 will be generally described as having a front face 11a which would be facing away from a test material, and a back face 11b which would be facing, or in contact with, a test material. The housing 11 also has at least one aperture 11c extending through the back face 11b. The aperture 11c is in a spaced apart relationship to the light source 12. When the apparatus 10 is in an "on" mode, the light passes through the aperture 11c and contacts a test material (as shown in FIG. 2).

The apparatus 10 also generally includes a power source 15a having an on/off switch 15b that is operatively connected to the light source 12. For example, the light exits from the back face 11b of the housing 11, while a power switch 15b for controlling the light source 12 can be located on the front face 11a of the housing 11. The apparatus 10 also includes other components, such as one or more electronic assemblies 16.

The apparatus 10 includes one or more resilient materials 14 that are positioned around, or in contact with, at least part of the light source 12. The resilient materials 14 are positioned protect the light source 12 from coming into undesirable contact with other components and/or the housing 11 of the apparatus 10. The resilient materials 14 are positioned to increase the mechanical reliability of the apparatus 10. During field use of the apparatus 10, if the apparatus is dropped or bumped, the light source 12 could be damaged due to shock waves hitting the light source from such impact. The addition of the resilient material 14 to one or more of the sides of (and/or adjacent to) the light source 12 protects parts of the light source 12 that may collide with a portion of the housing 11 or with other components and/or electronics assemblies 16 that comprise part of the apparatus 10.

Also, in certain embodiments, the apparatus 10 can be configured such that the light source 12 is secured in such a manner that one or more terminals 13 of the light source 12 are protected. In certain embodiments, rather than permanently soldering the terminals 13 to the electronic assembly 16, or firmly securing the terminals 13 in a locking mechanism (not shown), one or more implementing insertion sockets 18 are used in connection with the terminals 13. The insertion sockets 18 allow for slight movement of the light source 12 within the housing 11. The insertion sockets 18 aid in preserving the delicate construction of the light source terminals 13 and internal filaments of the light source 12.

In certain embodiments, the apparatus 10 can also include a protective covering material 20 to at least partially surround the housing 11 and provide additional shock absorption. The covering material 20 can be made of such useful shock absorbing materials such as elastomeric materials; synthetic rubber materials, silicone rubbers, neoprene, foamed neoprene, and the like.

For ease of explanation herein, the covering material 20 will be generally described as having a front face 20a which would be facing away from a test material, and a back face 20b which would be facing, or in contact with, a test material. The covering material also has at least one aperture 20 extending through the back face 20b. The aperture 20c is in a spaced apart relationship to the light source 12, and is in general alignment with the aperture 11c in the housing 11. When the apparatus 10 is in an "on" mode, the light passes through the aperture 20c and contacts the test material (as shown in FIG. 2).

Referring now to FIG. 2 along with FIG. 1, there is shown the apparatus 10 as generally including housing 11, light source 12, resilient materials 14, covering material 20, and an optional filter 19 positioned adjacent to the light source 12. The apparatus 10 is positioned adjacent a test material, shown herein as a glass "G" having a coated side, generally referred to herein as a tin side "TS," and a non-coated side "NS." The apparatus 10 is shown positioned for the viewing a fluorescing glow of the tin side TS of the glass G.

In certain embodiments, the actual viewing by the user can be improved significantly by having the covering material 20 be at least partially made of a material that allows the fluorescing visible glow (from the tin side TS of the glass G) to travel within the covering material 20.

In certain embodiments, the covering material 20 itself thus adds to the visual effect of the fluorescing. The human eye notices dramatic change in illumination much better than discerning between slightly different intensity levels. Therefore, when the covering material 20 changes color or shade due to the fluorescing light entering it, the user is able to discern Tin/Non-Tin side of the glass much easier.

It is to be understood that such covering material 20 can be made of (or have a coating of) a material that at least partially changes color when exposed to light. Non-limiting examples include photochromic materials that change from clear to colored when exposed to the fluorescing light. In such materials, the fluorescing light changes the chemical structure of the molecules so that it absorbs certain wavelengths of light (therefore making it appear as a color to our eyes). The more-fluorescing light absorbed, the more brilliant the color change. When the light source is removed, it reverts to a clear material. Other examples of useful photochromic materials include photo-chromic dyes and pigments that change color when exposed to specific wavelengths of light, i.e., activating light, and then revert to their original color when no longer exposed to these wavelengths. The color change may be from one color to another, or from a non-colored material to a colored material or vice versa.

Further, as it is generally understood that exposure of certain materials to types of light (e.g., UV light) can deteriorate such materials over time, it is within the contemplated scope of the present invention that the covering material 20 can be configured such that it can be easily replaced if any such deterioration or any damage is noticed.

Referring now to FIG. 3, there is shown another general diagrammatic embodiment of an apparatus 10 where the actual viewing by the user "U" can be improved significantly. For ease of explanation, components of the apparatus shown in FIG. 3 that are substantially the same as the components of the embodiment shown in FIG. 1, are given the same reference numeral.

In FIG. 3, there is shown the apparatus 10 positioned adjacent the test material, glass "G" having a coated side "TS" and a non-coated side "NS." The apparatus 10 is shown positioned for the viewing a fluorescing glow of the tin side TS of the glass G. The housing 11 of the apparatus 10 holds the light source 12 in a desired position. The housing 11 is generally configured to protect the user U from the UV-A, UV-B and UV-C light emanating from the UV light source 12. For example, the UV light exits from the back face 11b of the housing 11 through the aperture 11c, while the power switch 15b can be located on side that is opposite of the light. That is, power switch 15b controlling the light source 12 can be located on a front face 11b of the housing 11. When the apparatus 10 is in an "on" mode, the light emanates through the aperture 11c and contacts the test material G.

In the past, it was generally understood that, during use of an apparatus for detecting a tin side of a glass, the user often needed to angle the apparatus away from the glass slightly and look under the apparatus in order to see whether there was a fluorescing glow from the tin side, or whether there was a lack of glow (non-tin side).

Referring again to FIG. 3, the embodiment of the apparatus 10 shown therein overcomes such drawback. It is to be understood that, as the light from the light source 12 contacts the coated side TS, at least certain amounts of such light is reflected in different directions and can be seen as a fluorescing glow. The apparatus 10 shown in FIG. 3 includes at least one reflective surface 30 placed within the housing 11. The reflective surface 30 can be, for example, mirrors, prisms, fiber optics or any other reflective medium, or any combination thereof. The reflective surface 30 is placed in the housing 11 at an angle α to an optical path of the fluorescing glow/light which is being reflected from the coated side TS of test material G. For ease of illustration, an arrow Z is shown in FIG. 3 a indicating a path of certain reflected fluorescing glow/light. Such reflected light Z contacts, and is further reflected by, the reflective surface 30.

In the embodiment shown, one reflective surface 30 is at a 45° angle with respect to a plane A defined by the back face 11b of the housing 11. The reflected fluorescing glow/light Z is be directed out of the housing 11 through a viewing window 11d in the front face 11a of the housing 11 where such reflected fluorescing glow/light Z can be readily viewed by the user U. In certain embodiments, the viewing window 11d can have a graphical representation or area 11e which only allows certain of the light to exit. For example, the graphical area 11e could read "TIN SIDE."

By having the fluorescing glow/light Z be reflected back to the user U, the apparatus thereby allows the user U to safely and clearly view the results (i.e., fluorescing glow/light Z) from the back face 11a of the apparatus 11.

In certain embodiments, in order to reduce the number of components comprising the apparatus, the reflective surface 30 can be replaced with a prism that directs the fluorescing glow/light light to the user. In certain preferred embodiments, the transfer of light into the prism can be enhanced with a suitable interface material that has a similar index of refraction (for example, silicone), thereby lessening the loss of directed light.

In certain embodiments, the reflective surface 30 can be preferably made of a material where light is reflected from a first-surface in order to reduce any reflection loss. Non-limiting examples include a mirror or polished highly reflective material, such a metal material. It is to be understood that the mirror can be a plane mirror, which has a flat surface, or a curved mirrors, which focuses light.

Referring again to FIG. 3, there is shown an embodiment which includes an additional reflecting surface 30' that is positioned within the housing 11 to aid in capturing/reflecting the fluorescing glow/light being reflected from the coated surface TS. The one or more additional reflecting surfaces 30' can be positioned to direct such reflected fluorescing glow/light Z toward the reflective surface 30, and thus out of the housing 11 for viewing by the user U. While one additional reflective surface 30' is schematically illustrated in FIG. 3, it is to be understood that additional reflective surfaces can be positioned within the housing 11 for capturing additional reflected fluorescing glow/light Z.

Referring now to FIG. 4A, there is shown one embodiment of the back face 11b of the housing 11 that includes a display feature 40 for enhancing the fluorescent detection by the user. The display feature 40 can be accomplished by using an open area 42; for example, a stenciled or patterned area. In the embodiment shown in FIG. 4A, the words "TIN SIDE" may be provided in the display feature 40. The display feature 40 can be positioned in front of the housing aperture 11c (see FIG. 3) and behind the covering material aperture 20c, through which the light passes emanates. In such embodiment, the light from the light source 11 would only be allowed to pass through the stenciled area 42 of the display feature 40.

Referring now to FIGS. 4B and 4C along with FIG. 4A, it can be seen that, during use, a portion (labeled as reflected light "R" in FIG. 4C) of the light emanates from the fluorescing TS of the glass. This fluorescing glow/light R will project stenciled image I onto the tin surface TS of the test material glass G. That is, the UV light hits the tine side coating. The fluorescing light will go in both directions—back towards the UV light source and into the glass. The light that goes into the glass provides the image of TIN SIDE the observer sees in the end of the glass.

(It is to be understood, of course, in cases with an absence of any coating material, there would be no image projected onto the test material G).

In addition, the fluorescing glow/light R is refracted internally within the test material glass G. The fluorescing glow/light R within the glass is refracted ("bounces or travels") through the test material glass G, resulting in the stenciled image 42 appearing on an edge "E" of the test material glass "G" (see FIG. 4B). It should be noted that a glowing stenciled image would also be visible on the back side of the test material glass G, as well as under the apparatus, if the user were to lift an edge of the apparatus and look underneath it.

Referring now to FIGS. 5A and 5B, there is shown another general diagrammatic embodiment of an apparatus 10 where the actual viewing by the user "U" can be improved significantly. For ease of explanation, components of the apparatus shown in FIGS. 5A and 5B that are substantially the same as the components of the embodiment shown in FIG. 1 and FIG. 3A, are given the same reference numeral.

In the embodiment shown in FIGS. 5A and 5B, the apparatus 10 can be configured such that the covering material 20 has a slot 24 that allows at least a portion of a test material to be inserted into the slot 24. As shown by the side-elevational view of FIG. 5B, the slot 24 can be located on a side wall 26 of the covering material 20 that is at an angle with respect to the light source 12 within the housing 11. In certain embodiments, the housing 11 can be configured such that there is also a slot that is in alignment with the covering material slot 24, through which the test material can be positioned for inspection.

In use, the test material is inserted into the slot 24, and the light source is turned "on." The covering material 20 and/or the housing 11 thus substantially surround the portion of the test material that is now adjacent to the light source 12, thereby substantially blocking/removing much of the external or ambient light from disrupting the detection of any fluorescing glow/light.

Still further, in certain embodiments, as shown in FIGS. 6A-6D, the apparatus 10 can be configured whereby the housing 11 and/or covering material 20 define a defined area 40 at least partially surrounding the light aperture 11c and aperture 20c. The defined area 40 has edges that are close in proximity to the light source aperture, helping to form a "framed" definitive edge to the fluorescing glow/light. FIG. 6A is a schematic illustration showing a black viewing area 40 that is significantly larger than the light source 12. FIG. 6B is a side-elevational view of the embodiment of FIG. 6A, showing covering material thickness, schematically illustrating the UV light side emanated from the apparatus.

FIG. 6C is a schematic illustration showing a black viewing area 40 that is close in size to the size of the light source 12. In such embodiment, more fluorescing light enters the covering material 20 such that the user sees a greater change in color, shade and/or intensity of light. FIG. 6D is a side-elevational view of the embodiment of FIG. 6C, showing covering material thickness, schematically illustrating the UV light side emanated from the apparatus.

Still further, in certain embodiments, as shown in FIGS. 7A-7D, the apparatus 10 can be configured whereby the power to the light source 12 is pulsed, causing the difference between the fluorescing glow and lack thereof to be easier to detect with the eye. The pulsing power can occur by either continual pushes of a convenient momentary power switch, or by pulsing the power through microprocessor control. FIG. 7A is a schematic illustration showing the light source in an "on" mode, causing the fluorescing glow/light to enter the cover near the light source. FIG. 7B is a side-elevational view of the embodiment of FIG. 7A, showing the covering material 12 thickness and schematically illustrating the UV light side emanated from the apparatus. FIG. 7C is a schematic illustration showing the light source in an "off" mode, showing no fluorescing glow/light entering the cover near the light source. FIG. 7D is a side-elevational view of the embodiment of FIG. 7B, schematically illustrating that the color and/or shading of the covering material is generally uniform.

It is to be understood that, in certain embodiments, the apparatus described herein can contain one or more of the features described herein. For example, to improve the reliability of the apparatus in real life situations the shock-absorbing resilient materials can be added to any side of the light source that may come in contact with a portion of the housing or mounting mechanism (not shown) when jostled, bumped or dropped. Another feature includes where the light source terminals are connected to a power source (not shown) via insertion cups. The insertion cups allow the light source terminals to move when the apparatus is physically shocked, but still maintain electrical connection. Yet another feature includes the at least partial enclosure of the apparatus with a covering material, such as a shock-absorbing material to absorb shockwaves. In one preferred embodiment, the covering material is comprised of a silicone rubber material. In certain embodiments, all of these features work in conjunction to allow the light source to have free movement within a shock absorbing system. In particular, the resilient materials supporting the light source and the insertion cups work in concert to accomplish the shock absorbing task at hand.

Also, in certain embodiments, the apparatus as described herein can also include a protective covering that is at least partially comprised of (or coated with) a material that illuminates in the visible light fluorescing glow of the tin surface, making it easier for the user to differentiate the fluorescing glow from the non-fluorescing glow. The covering material will allow the fluorescing light to be absorbed, causing the covering material to change shade or color. The differential in color change in the material surrounding the viewing window versus material that is further away from the light aperture will be easier for the human eye to detect.

Still further, in certain embodiments, the apparatus can be configured to allow viewing of the glowing image of the tin surface which is transferred through the glass substrate and viewed in the edge surface of the glass. In this example, the words TIN SIDE would appear to glow on the edge surface of the glass.

Still further, in certain embodiments, the apparatus can be configured whereby the glowing image of the tin surface is transferred via mirrors, prisms, fiber optics or any other reflective medium, (or any combination of the aforementioned methods) to be projected back to the front face of the apparatus to be easily viewed by the user. Additional materials may be placed in the optical path of the light to better match the index of refraction of the glass to that of the prism or other optics.

While the invention has been described with reference to a preferred embodiment, it should be understood by those skilled in the art that various changes may be made and equivalents may be substituted for elements thereof without departing from the essential scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

What we claim is:

1. An apparatus for detecting a fluorescing substance on a test material, comprising:
    a light source configured to direct light energy toward a test material having thereon a fluorescing substance, and
    at least one display feature capable of being viewed through a viewing window in the apparatus, the display feature being configured to display fluorescing light from the test material and to project a fluorescing glow through the viewing window into an ambient environment when light from the light source contacts the fluorescing substance on the test material, wherein the display feature capable of being viewed through a viewing window in the apparatus, the display feature being is at least partially comprised of, and/or is at least partially coated, with a material that illuminates when exposed to fluorescing light.

2. The apparatus of claim 1, wherein the display feature includes an open area positioned adjacent to the light source for providing a pattern to the fluorescing glow.

3. The apparatus of claim 1, wherein the display feature is configured to allow light to be projected onto and/or through the test material.

4. The apparatus of claim 3, wherein the display feature is configured to allow viewing of the fluorescing glow in an edge surface of the test material.

5. The apparatus of claim 1, further including one or more reflective surfaces positioned at an angle with respect to the fluorescing light in order to project the fluorescing light to a front face of the display feature.

6. The apparatus of claim 5, further including a reflective material placed in an optical path of the reflecting light which allows an index of refraction of the test material to be optically matched to an index of refraction of the test material.

7. The apparatus of claim 1, wherein the apparatus includes a light source aperture having defined edges that are adjacent to the light source aperture, the defined edges being configured to form a pattern to the fluorescing glow.

8. The apparatus of claim 1, wherein the apparatus includes a source of power operatively connected to the light source and capable of providing pulsed energy sufficient to cause a detectable difference between the fluorescing glow and a lack thereof.

9. The apparatus of claim 8, wherein the power source includes a momentary power switch and/or a microprocessor control.

10. The apparatus of claim 1, wherein the display feature comprises at least one shock-absorbing covering material.

11. The apparatus of claim 10, wherein the covering material is comprised of a silicone rubber material.

12. The apparatus of claim 1, wherein the test material having thereon a fluorescing substance comprises a tin surface.

13. An apparatus for detecting a fluorescing substance on a test material, comprising:
    a light source configured to direct light energy toward a test material having thereon a fluorescing substance, and
    at least one display feature capable of being viewed through a viewing window in the apparatus, the display feature being configured to display fluorescing light from the test material and to project a fluorescing glow through the viewing window into an ambient environment when light from the light source contacts the fluorescing substance on the test material, wherein the display feature capable of being viewed through a viewing window in the apparatus, the display feature being at least partially is comprised of, and or at least partially coated with, a material which allows fluorescing light to be absorbed, causing the material to change shade or color.

14. The apparatus of claim 13, wherein the material that at least partially changes color when exposed to light comprises a photochromic material that changes shade or color when exposed to the fluorescing light.

15. The apparatus of claim 14, wherein the photochromic materials include photo-chromic dyes and pigments that change color when exposed to specific wavelengths of light.

16. The apparatus of claim 14, wherein the color change is from one color to another, or from a non-colored material to a colored material, or vice versa.

17. An apparatus for detecting a fluorescing substance on a test material, comprising:
    a light source configured to direct light energy toward a test material having a fluorescing substance thereon;
    at least one display feature configured to display fluorescing light from the test material and to project a fluorescing glow into an ambient environment near the apparatus when light from the light source contacts the fluorescing substance on the test material;

one or more reflective surfaces within the apparatus positioned to project a fluorescent image to a front face of the apparatus; and a housing defining a light source aperture having defined edges that are adjacent to the light source aperture, the defined edges being configured to form a pattern to the fluorescing glow.

18. The apparatus of claim 17, including a source of power operatively connected to the light source and capable of providing pulsed energy, causing a difference between the fluorescing glow and lack thereof.

\* \* \* \* \*